United States Patent [19]

Rosenthal

[11] 4,252,797

[45] Feb. 24, 1981

[54] CORTICOSTEROID CALCIUM COMPOSITIONS AND TREATMENT OF RHEUMATIC DISEASES THEREWITH

[76] Inventor: Walter Rosenthal, 150 E. 74th St., New York, N.Y. 10021

[21] Appl. No.: 58,763

[22] Filed: Jul. 19, 1979

Related U.S. Application Data

[63] Continuation-in-part of Ser. No. 866,297, Jan. 31, 1978, abandoned.

[51] Int. Cl.³ .............................................. A61K 31/68
[52] U.S. Cl. .................................. 424/201; 424/236; 424/280; 424/240
[58] Field of Search ............... 424/236, 240, 243, 201, 424/280

[56] References Cited

U.S. PATENT DOCUMENTS

| 2,967,801 | 1/1961 | Clark | 424/236 |
| 3,833,622 | 9/1974 | Babcock et al. | 260/397.2 |

FOREIGN PATENT DOCUMENTS

| 899656 | 6/1962 | United Kingdom | 424/236 |

Primary Examiner—Elbert L. Roberts
Attorney, Agent, or Firm—Dayton R. Stemple, Jr.

[57] ABSTRACT

A dosage composition of corticosteroids with calcium and optionally vitamins B12, C and/or D for treatment of arthritis and other rheumatic disease.

21 Claims, No Drawings

4,252,797

CORTICOSTEROID CALCIUM COMPOSITIONS AND TREATMENT OF RHEUMATIC DISEASES THEREWITH

CROSS-REFERENCE

This application is a continuation-in-part of my co-pending application, Ser. No. 866,297, filed Jan. 31, 1978, now abandoned.

BRIEF SUMMARY

This invention relates to new and useful improvements in the treatment of arthritis and other rheumatic disease with a mixture or dosage composition of corticosteroids and calcium compounds to which may optionally be added vitamins B12, C and/or D.

PRIOR ART

From the beginning of the cortisone era—25 years ago—the use of 11-oxy-steroids for treating inflammatory conditions became widespread. Generally prednisone, an alcohol, is used orally, and prednisolone (or methyl-prednisolone), the corresponding ketone, is used for parenteral injections. These compounds are five times more effective than the natural cortisone and thus minimize toxicity problems.

Then, fluorinated derivatives of corticosteroids (e.g. triamcinolone, dexamethasone, paramethasone and betamethasone) came into use, which are three to five times more effective than non-fluorinated compounds, but are also more toxic. Their use must be carefully monitored to avoid side effects varying with each product and some physicians avoid or restrict their use.

By far the widest application of corticosteroids is in the field of rheumatic diseases such as arthritis, neuritis, muscular, and neuromuscular rheumatism. They are used orally, parenterally, and frequently, intra and peri-articularly, i.e., injections in and around joints and joint cavities.

Side effects vary and are dependent on the type and amount of the administered corticosteroid and relate to the metabolism of proteins, fats, and carbohydrates. The latter two are only affected by careless or excessive corticosteroid administration, but the protein metabolism, especially of the bones is frequently, if not always affected, even by moderate or infrequent administration. The protein matrix of the bone is reduced, followed by calcium loss, and can lead to osteoporosis, which by itself is a prominent occurence in all forms of arthritis and may be the principal reason therefore.

SUMMARY OF INVENTION

I have found that calcium compounds given simultaneously with corticosteroids give excellent results in the treatment of rheumatic diseases. Moreover, inflammation is reduced by calcium administration. Apparently, simultaneous administrations of corticosteroids and calcium compounds helps at least three conditions, namely, it (1) obviates deleterious effects of calcium depletion by corticosteroids, (2) obviates calcium depletion by sugar mobilization from corticosteroids, and (3) replaces calcium regularly depleted in the skeleton by arthritis and rheumatism.

I have observed in the treatment of several hundred rheumatic patients with conventional corticosteroids, with and without calcium compounds, that the combined compounds are strikingly more effective. It is estimated that the action with intra- and peri-articular injections of corticosteroids combined with calcium is two to three times more intense and three to four times more prolonged than with steroids alone. Also, the combination is more effective than steroids alone upon oral and intramuscular administration. Because of the increased effectiveness, toxicity and side effects are diminished, less frequent or eliminated.

DETAILED DESCRIPTION

In carrying out the instant invention, corticosteroid and calcium compounds are used in sequence or conveniently and preferably together in one preparation, either one or both in solution or in suspension. The solution or suspension may be partial. The menstruum can be aqueous or aqueous-saline, with or without aqueous anesthetic such as procaine, lidocaine, etc. Additional benefit can be obtained by adding vitamins B12, C and/or D preferably in suspension or emulsion, each of which facilitate calcium absorption and utilization.

Corticosteroid as used herein means any of the adrenal corticosteroid hormones isolated from the adrenal cortex or produced synthetically, and derivatives thereof that are used for treatment of rheumatic diseases, such as arthritis.

Calcium compounds as used herein are any non-toxic compounds having sufficient solubility and used to assimilate calcium into the blood stream. Specific compounds include the acetate, ascorbate, carbamate, chloride, gluconate, glycerophosphate lactate, lactophosphate, levulinate, pantothenate, phosphate, salicylate and succinate.

It has been found that the most frequently used prednisone (11-keto-dehydrocortisone) or prednisolone (11-oxy-dehydrocortisone) should be used with an equal amount of calcium for arthritis injections and half the amount of calcium is preferably for neuritis injections. The fluorinated steroids require four to five times the weight of calcium. In the case of oral medication, it has been found advisable to use at least ten times the weight of calcium. These weight comparisons are based on the total weight of the steroid compounds but only the pro rata calcium portion of the calcium compound. For example, 5 mg of prednisone as the preferred corticosteroid in tablet form takes 50 mg of calcium, which is about 500 mg of calcium gluconate.

As to the individual calcium compounds, the inorganic salt generally used in medicine is calcium chloride, which is, however, an irritant and liable to cause tissue necrosis. The preferred embodiments are thus calcium salts of organic acids, which I have classified into low, medium and high solubility in water. The low solubility group, (up to 1%) is of limited value because of the relative insolubility.

The medium solubility group, (1 to 4%) such as calcium benzoate, -fumarate, -glycerophosphate, -gluconate, -lactate, -maleate, and -salicylate are highly suitable.

The high solubility group, (over 4%) such as calcium-acetylsalicylate, -quinate, glucoheptonate, -levulinate are also suitable but presently lack detailed physiological data.

Several of the mentioned calcium salts have the property of forming stable supersaturated solutions. Calcium gluconate, with which the majority of clinical trials was performed, is only soluble at the rate of 3.5%, but supersaturated stable 10% solutions have been used in medicine for many years.

The invention is not in a particular cortisone or calcium compound but the combination of any conventional cortisone and calcium compound. The compounds listed herein should be considered as suitable examples for carrying out this invention, but are not to be construed as limitations. Other calcium compounds or steroids could also be used whether presently known or later discovered.

The steroids, with their known toxicities, must be monitored and are thus given primary consideration for dosage level. Based on hydrocortisone as 1, the potency of the other are about prednisone and prednisolone 4, methyl-prednisolone and triamcinolone 5, paramethasone 10, and betamethasone and dexamethasone 25. The following table outlines dosage levels and frequency of the steroids.

| Steroid | Route | Dosage in Mg Range | Prefer | Frequency |
|---|---|---|---|---|
| Prednisone | Tablet | 4–15 | 5 | 1–3 daily |
| Prednisolone CH$_3$ | Tablet | 3–14 | 4 | 1–3 daily |
| Prednisolone | Injection | 15–40 | 25 | 1–2 weekly |
| Triamcinolone | Injection | 15–40 | 25 | 1–2 weekly |
| Paramethasone | Injection | 8–20 | 12.5 | 1–2 weekly |
| Dexamethasone | Injection | 3–9 | 5 | 1–2 weekly |
| Betamethasone | Injection | 3–9 | 5 | 1–2 weekly |

The weight of available calcium is then based on the amount of steroid and should be approximately equal thereto for injectable prednisolone and triamcinolone, two times greater for injectable paramethasone, five times greater for injectable dexa- and beta-methasone, and ten times greater for any tablets or other oral ingestion, any of these amounts of calcium being subject to ±50%. Since calcium toxicity is relatively nil compared to steroids, excess calcium may be used without harm but also without much increased benefits.

The vitamin dosage is conventional per dose, i.e., 0.5 mg B12, 50 mg C and 500 units D with ranges for B12 and C at ±50% and D at 200–1000 units. The calcium and/or vitamins may be supplied in sequence or simultaneously with the steroids in other dosage mediums, natural or synthetic and particularly orally (partially or completely) when the steroid is by injection.

I claim:

1. An anti-inflammatory preparation comprising pharmaceutically effective amounts of (a) 11-oxy corticosteroid compounds and (b) a compound having physiologically available calcium.

2. The preparation of claim 1 wherein said corticosteroid compounds are synthetic.

3. The preparation of claim 2 wherein said corticosteroid compounds are prednisone, prednisolone, methyl prednisolone, triamcinolone, para-, beta-, or dexa-, methasone.

4. The preparation any of claims 1 to 3 wherein said calcium compounds are organic acid salts.

5. The preparation of claim 4 additionally comprising pharmaceutically effective amounts of vitamins B12, C and D.

6. The preparation of claim 4 additionally comprising pharmaceutically effective amounts of vitamin C.

7. The preparation of claim 4 additionally comprising pharmaceutically effective amounts of vitamin D.

8. The preparation of claim 4 additionally comprising pharmaceutically effective amounts of vitamin B12.

9. The preparation of claim 4 dissolved in an anesthetic solution.

10. The preparation of claim 4 comprising a solution of 15–40 mg prednisolone and sufficient calcium gluconate to provide 50–150% by weight of calcium relative to the steroid.

11. The preparation of claim 4 comprising a solution of 3–9% mg dexamethasone and sufficient calcium levulinate to provide 250–750% by weight of calcium relative to the steroid.

12. The preparation of claim 4 comprising a tablet of 4–15 mg prednisone and sufficient calcium glycerophosphate to provide 750–1500% by weight of calcium relative to the steroid.

13. The treatment of arthritis in humans comprising introducing the compounds any of claims 1–3 into the body.

14. The treatment of arthritis in humans comprising introducing the compounds of claim 4 into the body.

15. The treatment of arthritis in humans comprising injecting intra-articularly the compounds of claim 9.

16. The treatment of arthritis in humans comprising injecting intra-articularly the compounds of claim 10.

17. The treatment of arthritis in humans comprising injecting peri-articularly the compounds of claim 9.

The following table demonstrates different dosage levels and excepients of this invention.

| Example | 1 | 2 | 3 | 4 | 5 | 5 | 7 | 8 | 9 |
|---|---|---|---|---|---|---|---|---|---|
| Prednisolone | 25 mg | 25 mg | | | | | | | |
| Prednisolone 2.5% suspension | | | 1cc | | | | | | |
| Methyl prednisolone | | | | | | 4 mg | | | |
| Prednisone | | | | | 5 mg | | | | |
| Dexamethasone | | | | 6 mg | | | | | |
| Triamicinolone | | | | | | | | 20 mg | |
| Paramethasone | | | | | | | | | 10 mg |
| Betamethasone | | | | | | | 6 mg | | |
| Calcium gluconate | 250 mg | 250 mg | 25 mg | | | | 250 mg | | |
| Calcium levulinate | | | | 150 mg | | 300 mg | | 150 mg | |
| Calcium glycerophosphate | | | | | 200 mg | | | | 200 mg |
| Vitamin B12 | 0.5 mg | | | | | | 0.5 mg | | |
| Vitamin C | 50. mg | | | | | | | 50 mg | |
| Vitamine D | 1000 | | | | 1000 | | | | |
| Lidocaine 1% solution | to 10cc | | to 10cc | to 10cc | | | to 10cc | to 10cc | to 10cc |
| Water or Saline | | to 10cc | | | | | | | |
| Powder Excipient | | | | | 100 mg | 100 mg | | | |

*Weight refers to actual amount of steroid or calcium in dosage, whereas, volume rfers to amount of the solution or suspension including carrier, etc. Vitamin D expressed in units. For knee joint cavity injection, the lidocaine makes up only to 5cc as the cavity cannot take 10cc. Concentration of solids in solution is thus double the 10cc make up.

18. The treatment of arthritis in humans comprising injecting peri-articularly the compounds of claim 10.

19. The treatment of arthritis in humans comprising injecting intramuscularly the compounds of claim 9.

20. The treatments of arthritis in humans comprising injecting intramuscularly the compounds of claim 10.

21. The treatment of arthritis in humans comprising orally ingesting the compound of claim 12.

* * * * *